United States Patent [19]

Wang

[11] 4,426,721
[45] Jan. 17, 1984

[54] X-RAY INTENSIFIER DETECTOR SYSTEM FOR X-RAY ELECTRONIC RADIOGRAPHY

[75] Inventor: Shih-Ping Wang, Los Altos, Calif.

[73] Assignee: Diagnostic Information, Inc., Sunnyvale, Calif.

[21] Appl. No.: 194,909

[22] Filed: Oct. 7, 1980

[51] Int. Cl.³ .................................... G03B 41/16
[52] U.S. Cl. ........................ 378/99; 250/213 VT; 250/366; 378/19
[58] Field of Search ............. 250/416 TV, 213 VT, 250/445 T, 366; 378/99, 19

[56] References Cited

U.S. PATENT DOCUMENTS

| | | | |
|---|---|---|---|
| 3,101,407 | 8/1963 | Shipman, Jr. | 250/416 TV |
| 3,937,965 | 2/1976 | Vasseur | 250/445 T |
| 4,031,396 | 6/1977 | Whetten et al. | |
| 4,051,378 | 9/1977 | Krippner | 250/445 T |
| 4,140,900 | 2/1979 | Wang | 250/213 VT |
| 4,166,957 | 9/1979 | Jäntsch | 250/445 T |
| 4,179,100 | 12/1979 | Sashin et al. | 250/416 TV |
| 4,187,430 | 2/1980 | Schmidt | |
| 4,203,037 | 5/1980 | Gur et al. | |
| 4,206,361 | 6/1980 | Hounsfield et al. | 250/445 T |

OTHER PUBLICATIONS

*McGraw-Hill Dictionary of Scientific and Technical Terms,* 2nd Ed., McGraw-Hill, 1978, p. 1205.
*Reference Data for Radio Engineers,* 4th Ed., Int. Tel. & Tel. Corp., New York, 1956, pp. 418-419.
J. A. Stein, "X-Ray Imaging with a Scanning Beam, 38 Radiology, vol. 117, pp. 713-716, Dec. 1975.
C. S. Katragadda et al., "Digital Radiography Using a Computed Tomagraphic Instrument," *Diagnostic Radiology,* vol. 133, pp. 83-87, Oct. 1979.
D. Sashin, et al., "Computer Electronic Radiography for Early Detection of Vascular Disease," *Proceedings of SPIE,* vol. 173, pp. 88-97, 1979.

*Primary Examiner*—Alfred E. Smith
*Assistant Examiner*—T. N. Grigsby
*Attorney, Agent, or Firm*—Philip M. Shaw, Jr.

[57] ABSTRACT

The apparatus of the invention includes a planer, proximity type x-ray image intensifier for detecting a fan beam of x-rays and for producing an intensified output visible light image on an output display screen which is sensed by a scannable, linear array of solid state diode detectors. In a first embodiment, a pair of side by side arrays are utilized to eliminate the effects of flare in the display screen. One of the linear arrays looks at the line signal on the output screen and the second linear array looks at a location on the output screen which is adjacent and parallel to the line signal. A net signal is derived by subtracting the signals from adjacent elements of the two parallel arrays so that signal flare in the image intensifier tube is removed. In a second embodiment, display screen flare is eliminated by covering the vacuum side of the display screen with metal having a thickness sufficient to dissipate one third of the kinetic energy of photoelectrons passing through it.

23 Claims, 16 Drawing Figures

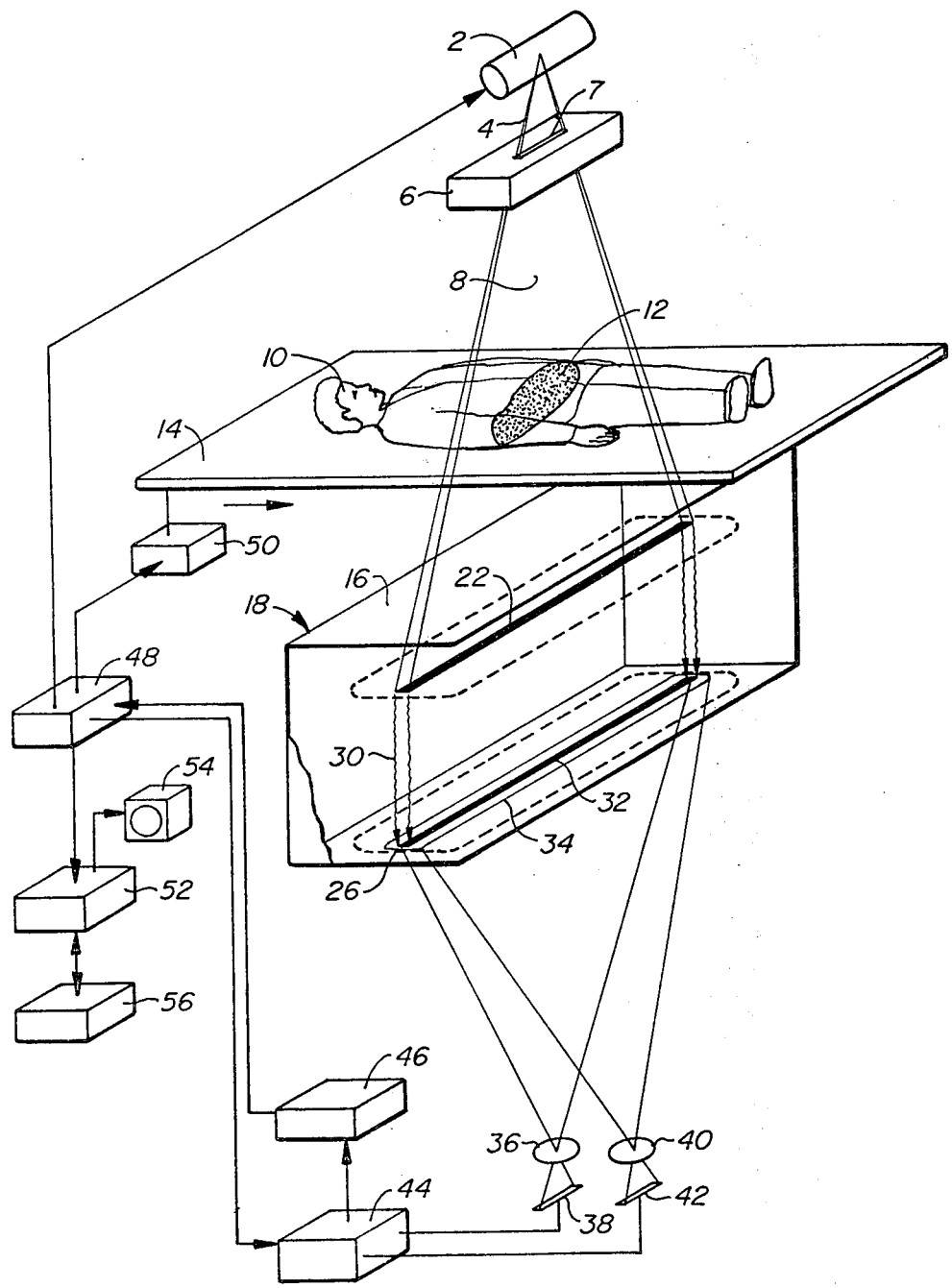
FIG._1.

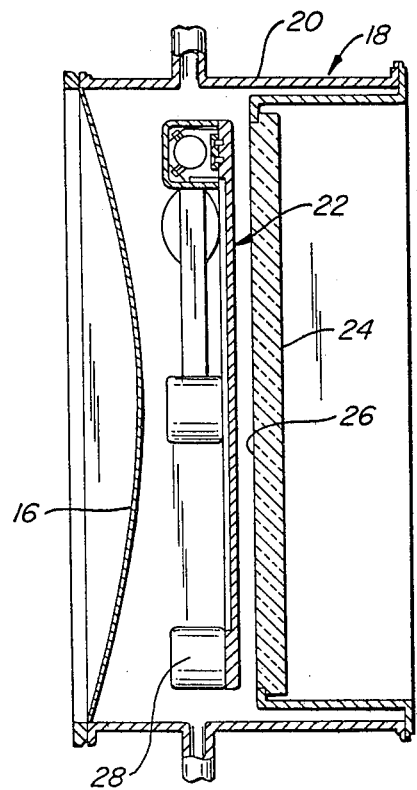
FIG._2.
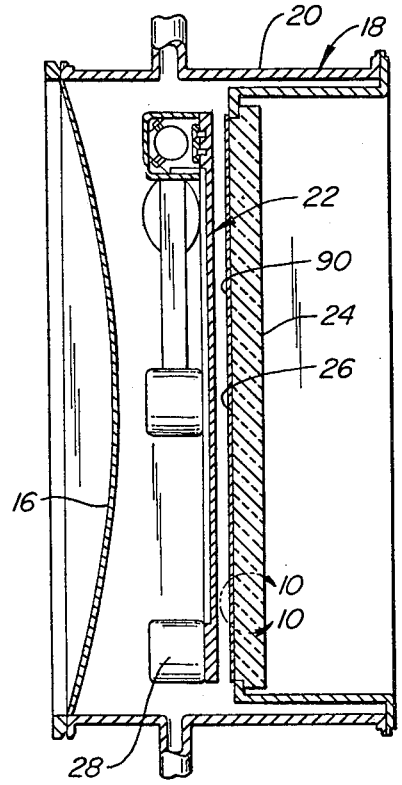
FIG._9.
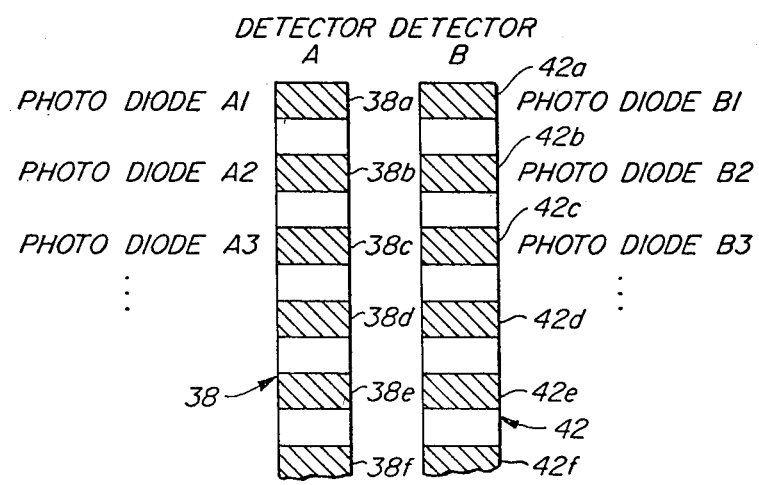
FIG._3.

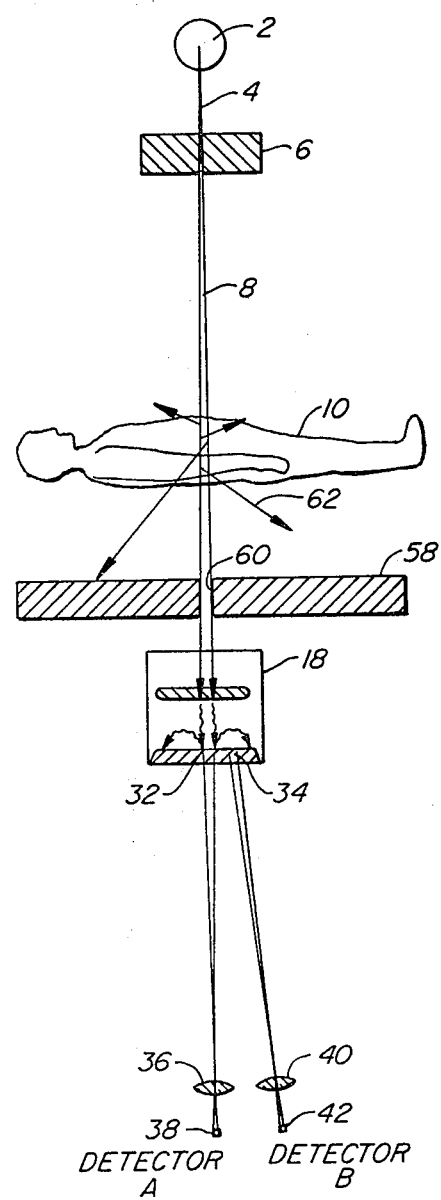
FIG._4.

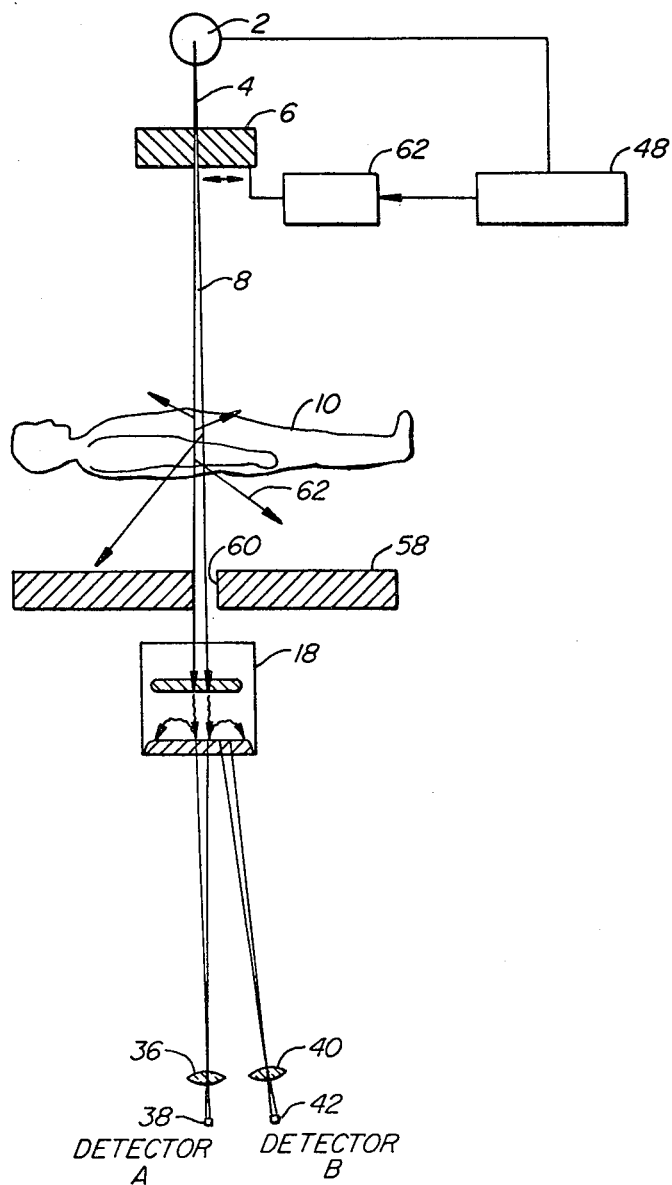
FIG._5.

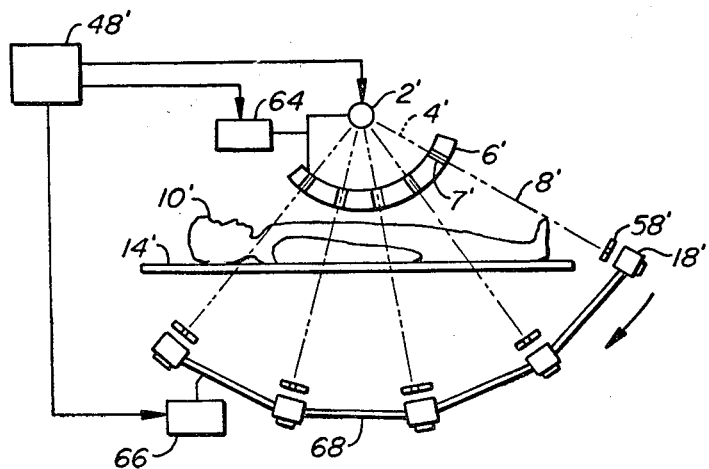
FIG._6.
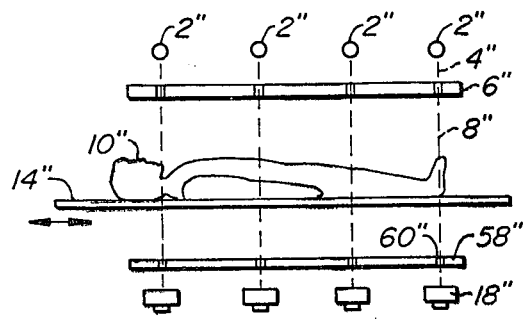
FIG._7.
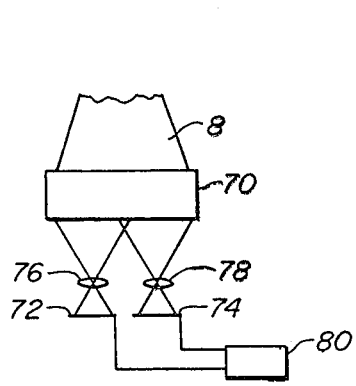
FIG._8.
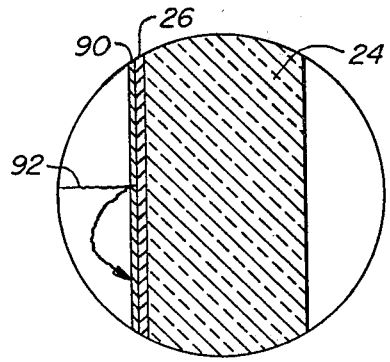
FIG._10.

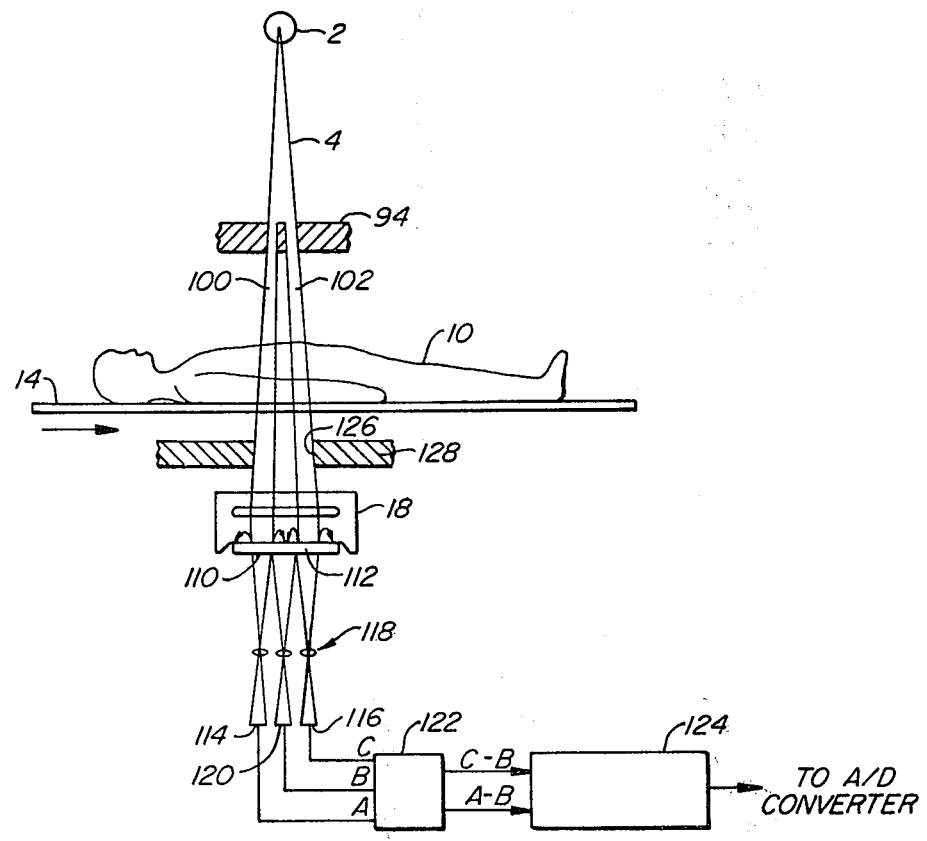
FIG.—12.

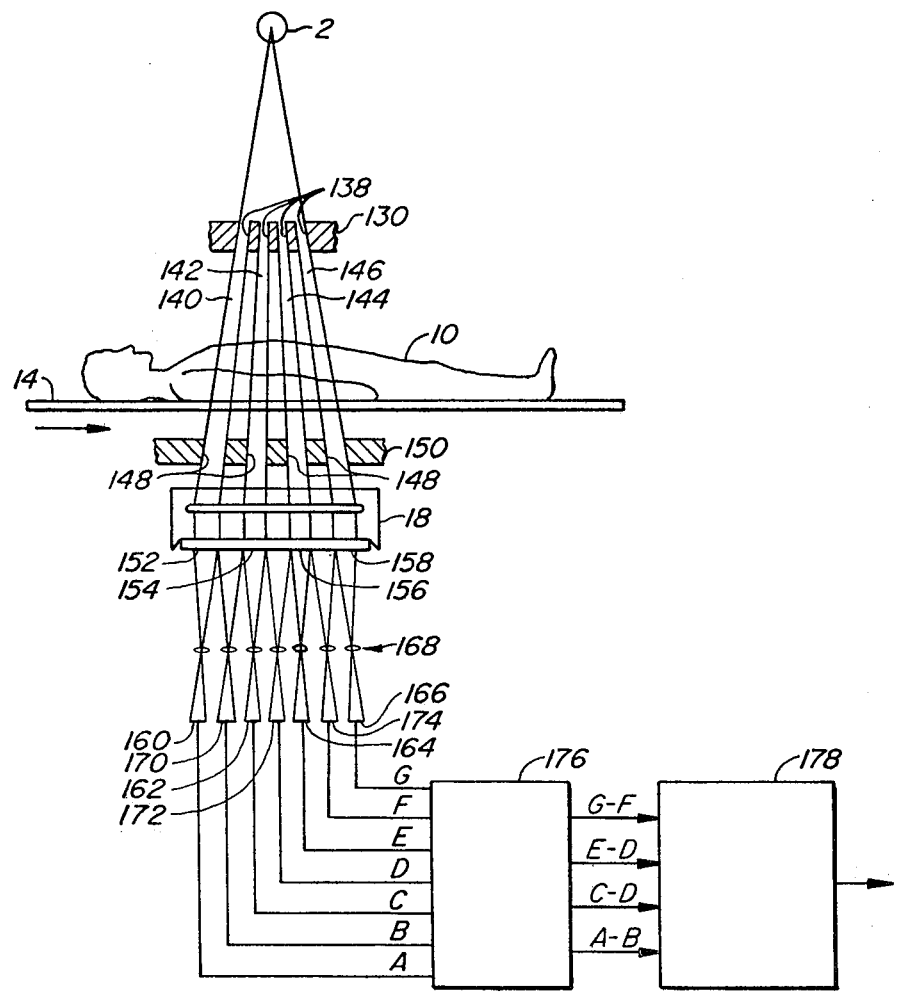
FIG._13.

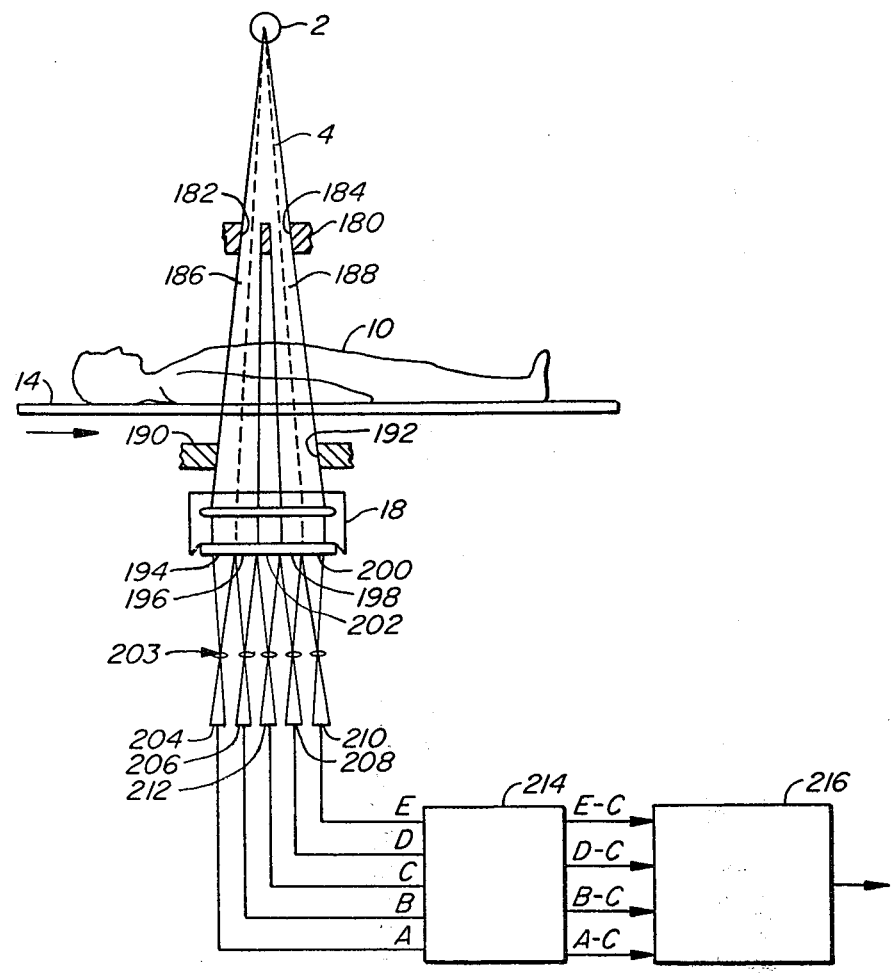
FIG._14.

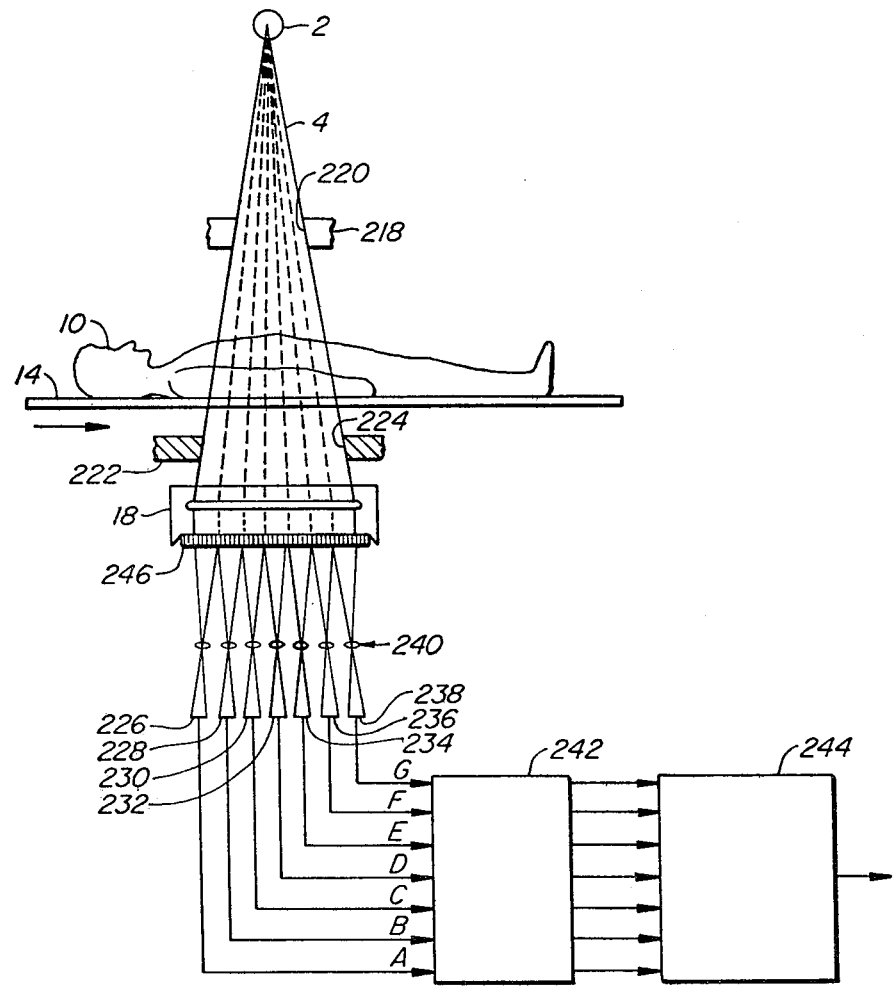
FIG._15.

X-RAY INTENSIFIER DETECTOR SYSTEM FOR X-RAY ELECTRONIC RADIOGRAPHY

BACKGROUND OF THE INVENTION

This invention relates to radiography apparatus adapted to provide improved contrast sensitivity while permitting reduced radiation exposure; more specifically, this invention relates to radiography apparatus employing a self-scanning array of photodiodes.

DESCRIPTION OF THE PRIOR ART

In recent years a number of improvements have been made in radiography systems which use reduced levels of radiation while providing improved images or image data of improved contrast sensitivity and detail; i.e. digital radiography systems. This has been accomplished by the use of electronic image enhancement systems operating in conjunction with self-scanned photo-diode arrays, as described in U.S. Pat. No. 4,179,100 (Sashin, et al.) and U.S. Pat. No. 4,203,037 (Gur, et al.).

The Sashin, et al. patent discloses a number of embodiments, the preferred ones of which utilize an x-ray fan beam which, after passing through the patient, impinges on a strip scintillator. The light pattern produced on the scintillator is focussed by means of an optical system onto a self-scanned photo-diode array and is then processed. The Gur, et al. patent further shows that the patient is moved relative to the fan beam to produce, line by line, a complete x-ray image of that portion of the patient which is being x-rayed. The electronic image thereby produced can be digitally enhanced to provide greater contrast sensitivity with reduced levels of radiation.

In one of the non-preferred embodiments of the invention described in the Sashin, et al. patent, an inverter type x-ray image intensifier tube is substituted for the scintillator strip and the photo-diodes are substituted for the phosphor display screen of the inverter tube. It is also suggested that the photo-diodes could alternatively be optically coupled to the image intensifier.

Other electronic radiographic systems utilize a linear array of discrete xenon gas cells which unfortunately have a spatial resolving ability limited to the neighborhood of 1.0 mm. While Sashin's system has a spatial resolving power much smaller than 1.0 mm., by using a continuous strip of scintillator material, only a very small portion of the light from the scintillator strip is collected by the lens, resulting in increased noise in the detector system, thereby forcing the detector system to operate at an increased x-ray dose level. While the use of an inverter type x-ray image intensifier tube helps in fully utilizing all the light produced by the scintillator, as mentioned in the Sashin patent, it is limited to systems wherein a small field size such as a disk of about 14 inches in diameter is involved. The size limitation stems from a number of factors, including the fact that such tubes are generally not commercially made in larger diameters. An additional problem arises in that the scintillator screen and the input face of the tube is reverse curved, thereby making it impossible for the scintillator screen to be in a parallel plane with the patient being x-rayed. This produces some distortion in the output image which is undesirable. Still another problem is that tubes of this type, due to their weak electrostatic focussing, are subject to exterior influences which may produce an untrue image.

One possible solution to many of these problems is to substitute a panel or proximity type x-ray image intensifier tube of the type described in U.S. Pat. Nos. 4,140,900 and 4,104,516 for the inverter type tube disclosed in the Sashin, et al. patent. One difficulty with such a substitution is that because such tubes do not use electrostatic or electromagnetic focussing, but instead accelerate the electrons from the photo-cathode screen directly to the phosphor output display screen, a certain amount of flare in the output image is thereby produced. This flare is produced in part by photo-electrons striking the phosphor display screen, rebounding and then again striking the phosphor display screen at points slightly displaced from the first point of impact, thereby producing a glow or flare of lower intensity around the primary image. This flare detracts from the contrast sensitivity which is sought to be achieved by the use of the self-scanned photo-diode array since the flare will also be picked up by the photo-diode array and will overlap the desired viewing image.

Still another problem for any type of electronic radiographic apparatus of this type is produced by patient scatter, that is, the x-ray radiation scattered by the patient into the detector system. While a number of mechanical devices have been employed to reduce this effect, such as collimators and grids, none of the prior art references known to the applicant suggest a way to electronically reduce patient scatter effects.

SUMMARY OF THE INVENTION

The above and other problems of electronic x-ray image intensifier radiographic systems are overcome by the present invention of an x-ray intensifier detector system for detecting an x-ray fan beam which system comprises an x-ray image intensifier tube having a continuous scintillator strip, a continuous photocathode strip, and a continuous output phosphor display screen strip for producing a light strip image representative of the x-ray pattern striking the scintillator. This image has a longitudinal axis of symmetry, and a first, scannable linear array of discrete light detectors sequentially detects light generated along the longitudinal axis of the display image.

In order to compensate for flare, in one embodiment a second, scannable linear array of discrete light detectors sequentially detects light generated on the display screen along a hypothetical line which is parallel to the longitudinal axis of the display image and which is spaced from it by a predetermined distance. The individual detectors of the first and second arrays have a physical correspondence which is determined, in part, by the sequence in which the detectors are scanned.

A scanning display is provided for displaying the individual differences between the outputs of the corresponding detectors of the first and second arrays. In this embodiment this involves scanning both arrays more or less simultaneously and subtracting the output of each detector of the second array from the output of each corresponding detector or detectors in the first array. This has the result of subtracting out the effects of the flare.

In modifications of this embodiment, since the spatial information is less in the flare region and is slower in varying than in the primary image region, the second array can have a coarser spatial resolution, that is, it can have larger elements, and a higher light sensitivity and therefore a lower noise sensitivity. In this arrangement, one element of the second array might correspond to two or more elements in the first array. This is particularly useful where the flare region has a lower signal level.

In still a further modification of the first embodiment of the invention, an asymmetric post scatter collimator slit is utilized. The purpose is to reduce the effect of the patient scattered x-rays in the plane of the fan beam which could enter into the detector system. In one embodiment the width of the post scatter collimator slit is twice that of the beam and the beam is placed asymmetrically to one side of the slit. The scattered x-rays therefore will spread equally across the slit, since the scatter distance (from the patient to the slit) is much larger than the slit width (typically less than 1.0 mm.). Therefore, the second photo-diode array will receive amounts of scatter which are equal to those received by the first photodiode array, and upon subtraction the net signal will contain very little of the effects of the patient scatter.

Still a further improvement in the preceeding embodiment of the invention is means for oscillating a pre-scatter collimator slit and at the same time pulsing the x-ray tube in synchronism so that the first and second detector arrays are alternatingly exposed. Subtracting the signal of the dark detector from the signal of the exposed detector to produce a net signal reduces the effect of any time lag characteristics which may be in the detector's system. Such time lag characteristics are sometimes produced by phosphor persistencies in the image intensifier.

In a second embodiment, flare is substantially eliminated by covering the vacuum side of the output phosphor display screen with a thick metallic layer, preferably of aluminum. The thickness of the layer is chosen to reduce the flare effect caused by rebounding electrons. The primary electrons, in creating the primary image at the output screen, go through the metallic reflective layer only once, whereas the rebounded electrons, in creating the flare, must go through the metallic reflective layer three times. Therefore, by making this metallic reflective layer sufficiently thick such that an incident electron has to expend about one-third of its kinetic energy in this layer in going through it, the rebounded electrons have to expend almost all of their kinetic energy in this metallic layer before striking the output phosphor screen again.

Typically for a proximity type x-ray image intensifier tube operating at 20,000 volts, the metallic layer penetration voltage is 6,000 to 7,000 volts. Aluminum is preferred as the metal due to its lower atomic number than the atomic number of the phosphor output screen, resulting in less Bremsstrallung.

Part of the flare in the image is casued by the light scatter in the output glass window. Therefore, a still further improvement is to substitute the output glass window with a thick fiber optical window.

While in the preferred embodiment a single fan beam is gnerated and the generator and the detectors are moved relative to the patient to complete a scan, in other embodiments a single generator generates several fan beams and each fan beam is coupled to a separate detector system so that the total system scan time or the x-ray generator tube's heat load or both are reduced by a factor equal to the number of fan beams used. Where a single generator is used to generate the multiple fan beams the whole system is rotated around the x-ray tube focal spot in a direction perpendicular to the planes of the fan beams. In other embodiments several x-ray generating tubes are placed next to each other, each generating a fan beam parallel to the other fan beams, and each fan beam being coupled to a separate detector system. Typically the patient or the x-ray system is then moved in a direction perpendicular to the fan beams to effect a scan. Again, the total scan time is reduced by a factor equal to the number of fan beams used.

A still further embodiment is a proximity image intensifier tube containing more than one strip of sensitive area parallel to each other so that more than one strip of image is intensified. This can be used with the multiple fan beam system or the patient can be indexed in synchronism with the scanning.

It is obvious that the system could be made to be curved and conforming to an arc in the plane of the fan beam with its center coincident approximately with the focal spot of the x-ray generator tube.

It is also obvious that more than one solid state array could be placed end-to-end in a line to provide more discrete elements to the detector. These arrays could each have their own lens system.

It is therefore an object of the present invention to provide radiography apparatus which provides improved contrast sensitivity and detail with a lower radiation dosage to the patient.

It is another object of the invention to provide a low noise level radiography apparatus which has a spatial resolving power smaller than 1.0 mm.

It is yet another object of the invention to provide an x-ray intensified radiographic detection apparatus which electronically compensates for signal flare in the intensifying detector.

It is a further object of the invention to provide radiography apparatus which electronically compensates for patient x-ray scatter.

It is yet a further object of the invention to provide radiography apparatus utilizing an x-ray image intensifier tube in which detector time lag is minimized.

It is yet a further object of the invention to provide radiography apparatus with multiple fan beams whereby the total scan time or the x-ray generator's heat load or both are reduced.

The foregoing and other objectives, features and advantages of the present invention will be more readily understood upon consideration of the following detailed description of certain preferred embodiments of the invention, taken in conjunction with the accompanying drawings.

BRIEF DESCRIPTION OF THE DRAWINGS

FIG. 1 is a diagrammatic, perspective view, partially in block form, of the detector apparatus according to the invention;

FIG. 2 is a detailed, vertical view, in section, of the image intensifier used in the apparatus of the invention;

FIG. 3 is a diagrammatic illustration of the photodiode array for use in explaining the operation of the invention;

FIG. 4 is a vertical, diagrammatic view of a modified, second embodiment of the invention;

FIG. 5 is a vertical, diagrammatic view of a modified, third embodiment of the invention;

FIGS. 6 and 7 are vertical, diagrammatic views of alternative, multiple detector fourth and fifth embodiments of the invention;

FIG. 8 is a diagrammatic, vertical side view of the detector arrangement of a sixth embodiment of the invention;

FIG. 9 is a detailed, vertical view, in section, of the image intensifier used in an eighth embodiment of the invention;

FIG. 10 is an enlarged, detailed view of the encircled portion in FIG. 10 with a diagrammatic tracing of an electron path; and FIGS. 11 through 15 are vertical, diagrammatic views of alternative, multiple beam, multiple detector sharing a single image intensifier tube embodiments of the invention.

DETAILED DESCRIPTION OF THE PREFERRED EMBODIMENTS

Figure 11:
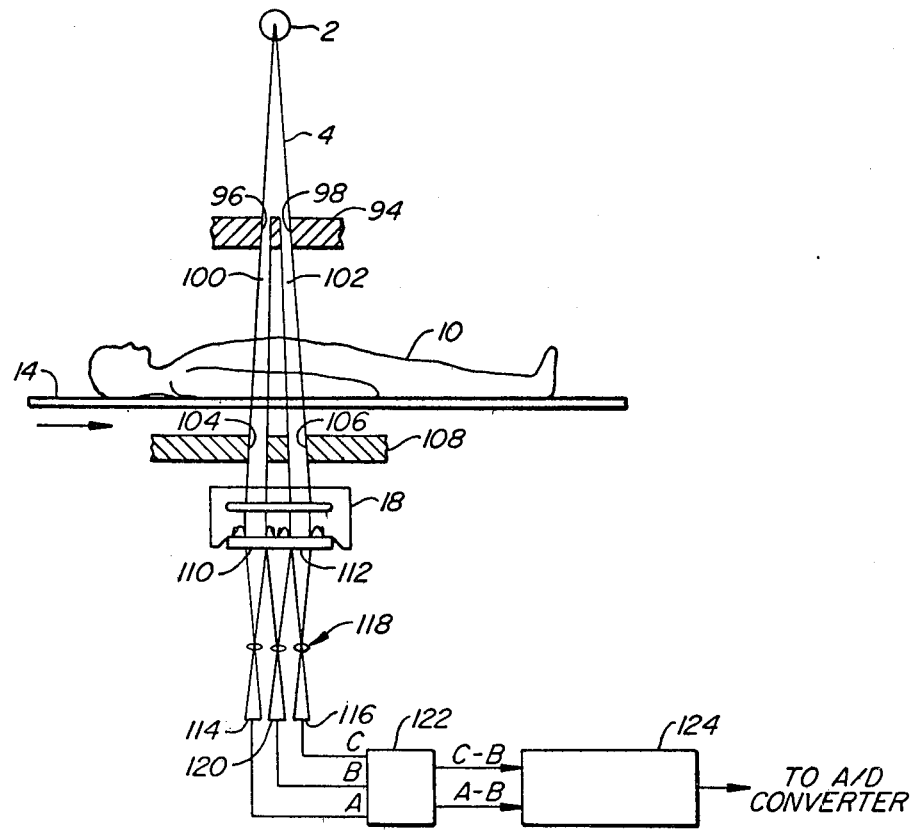

Referring now more particularly to FIG. 1, there is shown an x-ray generator, such as an x-ray tube 2, for generating a beam of x-rays 4 which impinge upon a pre-scatter collimator 6. The collimator 6 is preferably made of lead or other high atomic number material and contains a slit 7 which permits passage of a portion of the x-ray beam 4 therethrough. A fan-shaped x-ray beam 8 is thereby produced on the opposite side of the collimator slit 7.

This planar, fan beam 8 passes through a patient 10 to x-ray an area indicated by the shaded portion 12 in the Figure. The patient 10 is supported on a moveable table 14.

The x-ray fan beam, after passing through the patient, impinges on an x-ray transparent, input window 16 of a planar, proximity type x-ray image intensifier tube 18. The tube 18 is constructed essentially in accordance with the teachings in the applicant's issued U.S. Pat. No. 4,140,900 which is incorporated herein by reference. With particular reference to FIG. 2 of the present application, the tube 18 is comprised of the metallic input window 16 which closes one open end of a metallic housing 20. The opposite end of the housing 20 is closed by an output viewing window 24. On the interior surface of the window 24, with respect to the housing 20, is deposited a phosphor display screen 26. Intermediate the input window 16 and the display screen 26 is a scintillator-photocathode screen assembly 22. The screens 22 and 26 are planar and parallel to each other. The phosphor display screen 26 is in electrical contact with the tube envelope 20 and by means of electrodes 28, which support the scintillator-photocathode screen assembly and which are connected to an external, high voltage source (not shown), a high voltage electrostatic potential is applied between the photocathode portion of the scintillator-photocathode screen assembly and the phosphor display screen 26, all as described in greater detail in the aforementioned U.S. patent.

Referring again to FIG. 1, the x-ray fan beam 8 impinging on the scintillator portion of the scintillator-photocathode screen 22 produces a line image which is converted by the screen 22 into a corresponding pattern of photoelectrons 30 which are accelerated toward the output phosphor display screen 26 by means of the electrostatic potential between the two screens. The photoelectrons striking the phosphor screen produce an intensified line image 32 with a surrounding flare region 34. The line image has a longitudinal axis of symmetry.

The intensified line image 32 is optically focussed by means of a lens 36 onto a first linear photo-diode array 38. A portion of the flare region 34 along a hypothetical line which is parallel to the longitudinal axis of the display image and which is spaced from if by a predetermined distance, is focussed by means of a separate lens 40 onto a second linear self-scanned photo-diode array 42.

The photo-diode arrays 38 and 42, as mentioned, are of the self-scanning variety such as those manufactured by Reticon Corporation of Sunnyvale, Cal. These photo-diode arrays are described, among other places, in U.S. Pat. No. 4,179,100 and therefore will not be described in greater detail herein other than to state that each array should contain up to 1,024 diodes. A larger array in other embodiments is also feasible. Charge coupled photo-diode arrays could also be employed, although less advantageously for purposes of image enhancement.

The outputs of the arrays 38 and 42 are supplied to a diode control circuit 44 of the type described in U.S. Pat. No. 4,179,100. The control circuit 44 controls the simultaneous scanning of the two arrays 38 and 42 and also, by means of a differential amplifier circuit or the like, supplies an output signal which represents the signal difference between the arrays 38 and 42 on an element by element basis.

Referring now more particularly to FIG. 3, the elements 38a, 38b, etc. of the array 38 and the elements 42a, 42b, etc. of the array 42 are shown in diagrammatic form. As is clear from the figure, the elements of the array 42 have a physical correspondence to the elements of the array 38, i.e., they are aligned with it in the embodiment shown in FIG. 3. Thus, the element 42a is aligned with the element 38a and the element 42b is aligned with the element 38b, etc. The signal derived from the element 38a will represent not only the portion of the intensified line image 32 detected by the element 38a but also portions of the flare signal appearing at positions corresponding to the elements 38b, 38c, etc. Since the full width at half maxima (FWHM) of the flare is in the neighborhood of 50–200 times the size of each photo-diode element, each element sees flare from positions corresponding to a large number of elements (at least 50–200 of the elements).

The signal derived from photo-diode element 42a contains the same flare signal as that derived from photo-diode element 38a but with little or none of the signal derived from the intensified line image 32. Therefore, a simple formula for deriving the line image signal free of the flare signal is:

$$S_a = S_{38a} - S_{42a}$$
$$S_b = S_{38b} - S_{42b}$$
$$\vdots$$
$$S_n = S_{38n} - S_{42n}$$

where $S_a, S_b, S_o \ldots S_n$ = signals from successive photo-diode elements, flair free $S_{38a}, S_{38b}, S_{38c} \ldots S_{38n}$ = signals derived from successive elements of the photo-diode array 38

$S_{42a}, S_{42b}, S_{42c} \ldots S_{42n}$ = signals derived from successive elements of photo-diode array 42.

It is important to note that the flare is signal related, is not a general background noise and can only be compensated if the second photo-diode array is detecting a portion of the output screen which is much closer to the line signal image than the flare FWHM (full width at half maxima), or the flare distance. The FWHM of the line signal 32 could be in the neighborhood of 0.2–2 mm. depending on the intensifier tube design and on the collimator slit width selected. The FWHM of the flare 34 at the output screen of the tube could be typically 20–40 mm. Therefore, the placement of the area to be monitored by the detector array 42 is not too critical as long as it is placed at a distance equal to 1–10 times the FWHM of the line signal from the line signal.

In some embodiments it may be desirable to have more than one detector to monitor the flare for more precise flare compensation. In such embodiments the mathematics described above to compensate for flare may be more complex than a simple subtraction method. More precise formulation for flare compensation can be derived by carefully measuring the flare characteristics of these alternative embodiments. Also, although the two linear arrays are shown as separate elements in FIG. 1, which are separately lens coupled, in other embodiments it is possible to obtain a single solid-state chip with two parallel arrays on it so that only a single lens is needed to couple it to the output screen of the intensifier tube.

In still another embodiment, two solid state arrays with dissimilar characteristics are utilized. Since the spatial information is less in the flare region and is slower in varying, the solid state array corresponding to the array 42 can have a coarser spatial resolution, that is, it can have larger elements and a higher sensitivity, and therefore, a lower noise output signal. This is because a larger element gathers more light and tends to integrate the noise, with the result that the noise level is reduced. In this way, the subtraction process is more accurate, especially since the flare region has a much lower signal level.

Referring again to FIG. 1, the net difference output signal from the array control circuit 44 is supplied to an analog-to-digital (A/D) converter 46. The digital output signal from the converter 46 is supplied to an electronic control circuit 48. The control circuit 48 is connected to the x-ray tube 2, the array control unit 44, a motor drive 50, which moves the table 14 in a direction which is perpendicular to the plane of the fan beam 8, and to a display and memory unit 52. The purpose of the control unit 48 is to coordinate the operation of the x-ray tube 2, the motor drive 50 and the array control 44 so that all of these various elements are synchronized in their operation. The control unit 48 has manual control switches (not shown) for the use of the operator of the apparatus.

The display and memory unit 52 operates a raster scan graphic display and film print out unit 54 and the two units 52 and 54 may be any one of a wide variety of commercially available raster scan graphic displays such as the 9400 model graphic display system manufactured by Ramtek Corporation, for example. The display and memory unit 52 can, in the preferred embodiment, interface with a computer and a computer memory 56 which receives the signal data from the photo-diode arrays 38 and 42 for processing and analysis. Although the computer 56 can provide image enhancement capability, the display and memory unit 52, typically, also has this capability.

Referring now more particularly to FIG. 4, the x-ray beam 8 striking the patient 10 produces not only the desired x-ray signal but also produces patient-scattered x-rays 62. By providing a post-scatter collimator 58 having a slit 60, patient scatter striking the intensifier tube 18 is reduced.

Referring now more particularly to FIG. 5, the embodiment depicted in FIG. 4 is modified so that the slit 60 has a width which is equal to twice the width of the fan beam 8. The beam 8 is directed by the collimator 6 to one side of the slit 60 in an asymmetric manner. This reduces the effect of the patientscattered x-ray 62 in the plane of the fan beam which would otherwise enter into the detector system. The scattered x-rays 62 will spread equally across the slit, since the scatter distance, that is, the distance from the patient 10 to the slit 60, is much larger than the slit width (less than 1.0 mm.). Therefore, the flare region 34 monitored by the diode array 42 will receive the same amount of patient scatter as the signal region 32 monitored by the photo-diode array 38. Upon subtraction of the signals, as described above, the net signal from the array control 44 will contain very little of the effects of patient scatter.

Still a further improvement is to oscillate the pre-scatter collimator 6 and the slit 7 while simultaneously pulsing the x-ray tube 2 in synchronism. This is accomplished by means of a motor drive 62 connected to oscillate the collimator 6 and which is operated by the control circuit 48. In this way, the photodiode arrays 38 and 42 are alternatingly exposed. Subtracting the signal of the dark detector from the signal of the exposed detector to produce a net signal reduces the effect of any time lag characteristics which may be in the detector's system. Phosphor persistencies in the image intensifier tube 18 are common sources of such detector time lag.

Referring now more particularly to FIGS. 6 and 7, alternative embodiments are depicted in which several x-ray fan beams are simultaneously utilized in conjunction with a plurality of corresponding detectors. The elements which are common to the embodiments heretofore described have been given the same reference numerals primed. Relative motion of the x-ray in relation to the patient is simultaneously accomplished for all of the fan beams and the detectors so that the patient is simultaneously x-rayed in adjacent segments. The purpose of this arrangement is to reduce the amount of time that each x-ray generator must be turned on. While it is possible to x-ray the entire patient with only a single x-ray fan beam and a single detector, heat dissipation problems greatly shorten the life of the x-ray tube. Also, the time required to x-ray the patient is greatly reduced when multiple fan beams are utilized.

Referring particularly to FIG. 6, the x-ray source 2' generates a wide angle x-ray beam 4' which impinges on an annularly shaped collimator 6' having angularly spaced apart, radial slits 7'. The collimator 6' produces a plurality of radially extending fan beams 8'. These fan beams 8' are angularly spaced apart at regular intervals. After passing through the patient 10', the fan beams 8' impinge on post scatter collimators 58', which are angularly spaced apart and associated with separate detectors 18'. Each detector 18' includes an image intensifier tube of the type described above in reference to FIG. 1 and a pair of photo-diode arrays (not shown in detail) which operate in the manner described for the preferred embodiment. The detectors 8' are arranged along hypothetical lines which pass through the tube focal spot and are linked together by a framework 68.

A motor drive 64 connected to the pre-scatter collimator 6' and the x-ray tube 2' and a motor drive 66 attached to the framework 68, are operated by the control circuit 48' in unison so that the tube 2', the collimator 6' and the detectors 18' can all be rotated in synchronism in a clockwise direction as viewed in FIG. 6 to scan the patient 10'. This reduces the total system scan time by a factor equal to the number of fan beams used. The rotation is around the x-ray tube focal spot and is in a direction perpendicular to the planes of the fan beams 8'.

Referring now to FIG. 7, a plurality of x-ray generators 2" each generate x-ray beams 4" which are converted to parallel fan beams 8" by means of a collimator, or a plurality of collimators, 6". The fan beams 8" are plane-parallel to each other and pass through the patient 10" to impinge on a plurality of associated detectors 18" of the type herein above described. Fan beams 8" pass through post scatter collimator slits 60" in a combined collimator, or in a plurality of collimators 58". Relative movement is accomplished by moving the table 14", on which the patient 10" is supported, in a direction perpendicular to the planes of the fan beams 8".

Referring now more particularly to FIG. 8, the detector arrangement of a sixth embodiment of the invention is illustrated. The proximity image intensifier tube 70 is constructed substantially identical to the tube 18 described above in reference to the embodiment depicted in FIG. 1. The primary difference in this embodiment is that a pair of photo-diode detector arrays 72 and 74 placed end to end are used to detect the line output image on the phosphor display screen of the tube 70. A pair of lenses 76 and 78 focus portions of the line output image onto the arrays 72 and 74, respectively. As can be seen from the drawing, there is a finite amount of overlapping in the coverage of the lenses 76 and 78 in focussing on the line output image of the tube 70. This overlap is compensated for either physically by blocking out some of the photodiodes, or electronically, and the two arrays 72 and 74 are read sequentially by a control unit 80.

In this embodiment, either the diode arrays 72, 74 and 90 would include a second, flare compensating diode array of the type described above in reference to the embodiment of FIG. 1, or the output screen of the detector 18 would be provided with a suitable, flare reducing covering of the type now to be discussed.

While in the preferred embodiment a second photodiode array is utilized to compensate for flare, in still another embodiment of the invention a proximity x-ray image intensifier tube, of the kind described in reference to the embodiment of FIG. 1, is utilized which has a metallic reflective layer of predetermined thickness covering the vacuum side of the output phosphor display screen 26.

Referring more particularly to FIGS. 9 and 10, a metallic layer 90 is placed over the phosphor screen 26 on the vacuum side. This layer 90 is preferably chosen from a material having a lower atomic weight than the atomic weight of the phosphor output screen, thereby producing less bremsstrallung. The applicant has found aluminum to be a particularly satisfactory material. The thickness of the material is chosen to reduce the flare effect caused by rebounding electrons.

These rebounding electrons ordinarily strike the phosphor display screen, producing a light image, and then rebound into the vacuum space between the photocathode and the phosphor display screen. Because of the electrostatic field applied through the electrodes 28, the electrons are again attracted to the phosphor display screen at a point removed from their first impact and strike the phosphor display screen a second time to produce the flare effect discussed above. This is not a problem in conventional, inverter type tubes due to the difference in the electron optics.

Referring particularly to FIG. 10, if an incident electron 92 passes through the covering 90 to strike the phosphor display screen and then rebounds from the phosphor display screen it must again pass through the covering 90 twice more before it can again strike the phosphor display screen 26. The thickness of the covering 90 is chosen so that by the time the rebounding electron again strikes the phosphor display screen 26 all its kinetic energy has been dissipated and it does not produce a light image when it strikes the phosphor display screen 26 on the rebound.

The choice of thickness of the covering 90 is critical. If the film is not thick enough, the flare effect will not be corrected. On the other hand, too thick a covering will only reduce the tube gain without further reducing the flare.

The reason is that whenever an electron with energy $E$ passes through the covering 90 a certain amount of its energy $E_0$ is expended in the covering. This $E_0$ is sometimes called the breakthrough energy. Therefore, the useful energy of the transmitted electron is approximated by $(E - E_0)$. The brightness of the output screen is approximated by the formula $$B = k(E - E_0)N$$

where
B = brightness of the output screen in candela per square meter (Cd/m$^2$)
k = conversion constant of the screen in candela-second per electron volt (Cd-sec/ev)
E = kinetic energy of a single incident electron in electron volts (ev)
$E_0$ = energy loss in the covering by the single electron in electron volts (ev9
N = current density of the incident electrons in number of electrons per square meter-second (1/m$^2$-sec).

The flare brightness due to backscattered electrons in a proximity type image tube can be approximated by the formula $$B_s = \frac{k(E - 3E_0)N}{m^2}$$

where
B = brightness of the output screen due to the backscattered electrons in candela per square meter (Cd/m$^2$)
E = kinetic energy of a single incident electron in electron volts (ev)
$3E_0$ = the total energy loss in the covering 90 by the backscattered electron after tranversing the covering three times in electron volts (ev)
N = current density of the incident electrons in number of electrons per square meter-second (1/m$^2$-sec)
$\eta$ = dimensionless backscatter co-efficient ($0 < \eta < 1$)
m = dimensionless spread magnification factor equal to the ratio of the FWHM of flare spot spread distribution to the FWHM of spiral spot spread distribution.

It is found that as the covering 90 is made sufficiently thick such that $E_0 \sim 1/3E$, the flare effect due to the backscattered electrons becomes a small quantity. The tube gain for a single stage device is reduced to two-thirds and for a two stage device is reduced to about one-half.

The thickness of the covering 90 is related to $E_0$ by the following formula $$t = (k_1/\rho)(E_0)^{k_2}$$

where
t = covering thickness in centimeters (cm)
$\rho$ = density of covering in grams per cubic centimeters (gm/cm$^3$).
$E_0$ = energy loss of the electron in electron volts (ev)
$k_1$ = constant ($\approx 5.5 \times 10^{-11}$ gm/cm$^2$-ev for aluminum)
$k_2$ = constant ($\approx 1.65$ for aluminum).

Restating the optimum covering thickness in terms of the incident energy of the electrons:

$$t = (k_1/\rho)(E/3)^{k_2}$$

Using the above formula, for an 18,000 ev incident electron, the optimum aluminum film thickness is approximately 0.35 micron.

There are several ways to reduce the load on the X-ray generator tube 2 by using more than one fan bean simultaneously. Two such ways are shown in FIGS. 6 and 7 where multiple fan beams are separately coupled to multiple detector systems. Each point of the patient's body is scanned or visited by a single fan beam once. For example, if we imagine that there are 2000 lines marked on a patient's body parallel to the planes of the fan beams and perpendicular to the direction of scan, and that there are 4 fan beams as illustrated in FIGS. 6 and 7, then one fan beam would scan lines 1 through 500, the second fan beam would scan lines 501 to 1000, the third fan beam would scan lines 1001 to 1500 and the fourth fan beam would scan lines 1501 to 2000.

The slits of the pre-scattered collimators 6' or 6" in these cases, to a large extent, determine the line resolution or the vertical, spatial resolution (resolution along the scan direction). The wider the slit, the lower the spatial resolution.

In constrast to this system where multiple fan beams have multiple detectors, the embodiments depicted in FIGS. 11-15 have either a single fan beam or a plurality of fan beams which share a single proximity image intensifier tube detector system. Each point of a patient's body is scanned or visited by more than one fan beam or by a fan beam whose thickness exceeds the spacing between adjacent photo-diode arrays in the detector. The vertical, spatial resolution is determined more by the image intensifier of the detector system than by the slit width of the pre-scatter collimator. The finer the spatial resolution of the detector system, the better the vertical resolution.

Referring now to the embodiment depicted in FIG. 11, a single x-ray tube source 2 generates a fan beam 4, which impinges on a pre-scatter collimator 94 having a pair of parallel slits 96 and 98. These slits thereby produce a pair of parallel fan beams 100 and 102 which pass through the patient's body 10 supported on a movable table 14. After passing through the patient's body, the x-ray beams 100 and 102 pass through collimator slits 104 and 106 of a post-scatter collimator 108. The beams 104 and 106 impinge on an x-ray image intensifier tube 18 of the type described above in reference to the embodiment depicted in FIG. 1 and produce two output line images 110 and 112 on the output phosphor display screen.

These line images 110 and 112 are read by a pair of photo-diode arrays 114 and 116 through suitable optical means 118. A third photo-diode array 120 reads the flare region of both of the lines 110 and 112 through the optical means 118. The photo-diode arrays 114, 116 and 120 are controlled by a control circuit 122 which produces a pair of difference output signals. The first output signal corresponds to the difference between the output signals of the photo-diode array 114 and the photo-diode array 120. The second output signal corresponds to the difference between the output signals of the photo-diode array 116 and the photo-diode array 120. The table 14 is controlled by the motor drive 50 and control circuit 48 (FIG. 1) to index by a discrete amount each time an exposure is made by reading the photo-diode arrays.

Thus, if we imagine the patient's body as having 2000 hypothetical lines which run perpendicular to the direction of travel of the patient on the table 14 and parallel to the planes of the fan beams 100 and 102, line 1 on the patient's body would be scanned first by the fan beam 100. The patient's body would then be indexed by a discrete amount so that upon the next exposure reading, that is, the next time the photo-diode arrays are scanned, line 1 would be exposed to the fan beam 102. This process would continue until all the 2000 lines on the patient's body had been scanned by both of the fan beams 100 and 102.

The output signals from the controller 122 are supplied to a multiplexer and storage unit 124 which contains separate storage registers. When line 1 of the patient's body is scanned by the fan beam 100, the output signal of the difference between the outputs of the detectors in the photo-diode array 114 and the detectors in the photo-diode array 120 are stored in a register within the multiplexer 124. After the patient is indexed by the discrete amount, the net signal difference between the detectors of the photo-diode arrays 116 and 120 are added to the stored values in the multiplexer 124 to give a combined reading for a line 1. This process is repeated for each of the hypothetical lines on the patient's body. Since each line is scanned twice, the current for the x-ray tube 2, and therefore the heat load, can be reduced by half, that is, by the number of fan beams used, and still each line receives the proper exposure.

The above process is better illustrated by the following mathematical description. If the output signal from the photo-diode array for a given hypothetical line on the patient's body is designated S and the output signals from the photo-diode arrays 114, 120 and 116 are designated A, B and C respectively, then the output signals on a line-by-line basis are given by the following formula:

$$S_1 = (A_1 - B_1) + (C_2 - B_2)$$

$$S_2 = (A_2 - B_2) + (C_3 - B_3)$$

$$S_n = (A_n - B_n) + (C_{n+1} - B_{n+1})$$

where $S_n$ is the total signal from the nth pypothetical line on the patient's body. $A_n$, $B_n$ and $C_n$ are the signals from A, B, and C respectively at the nth exposure. After each exposure the patient's body is indexed and moved exactly by the distance separating the adjacent fan beams.

Referring now more particularly to FIG. 12, basically the same arrangement is illustrated except that the post-scatter collimator 128 only has a single slit 126 which is sufficiently wide to allow both fan beams 100 and 102 to pass through it. Thus, the detector 120 is exposed to the patient's scatter.

Referring now more particularly to FIG. 13, the x-ray fan beam 4 from the tube 2 is divided into four fan beams 140, 142, 144, and 146 by a prescatter collimator 130 having four, parallel, spaced-apart slits 138. The multiple fan beams 140–146 pass through the patient's body 10 and through corresponding slits 148 in a post-scatter collimator 150 to strike the input surface of an image intensifier tube 18 of the type described above with reference to the embodiment depicted in FIG. 1.

Four separate line images 152, 154, 156 and 158 are thereby produced on the output screen of the image intensifier 18. These line images are focused by suitable optical means 168 onto four separate photo-diode arrays 160, 162, 164 and 166, respectively. The flare region correponding to the line image 152 is sensed by a photo-diode array 170 and the flare regions corresponding to the line images 154 and 156 are sensed by a photo-diode array 172. The flare region corresponding to the line image 158 is sensed by a photo-diode array 174.

The net difference between the outputs of the corresponding elements in the photo-diode arrays 160 and 170 is supplied to a multiplexing circuit 178. The net difference between the outputs of the corresponding elements of the photo-diode arrays 162 and 172, and between the photo-diode arrays 174 and 172 are also supplied to the multiplexing circuits 178. The same is true for the net difference between the photo-diode arrays 166 and 174.

The output of the multiplexing circuit 178 is supplied to the A and D converter 46 of the system depicted in the embodiment of FIG. 1. If the output signal from the photo-diode array for a given hypothetical line on the patent's body is designated S and the output signals from the photo-diode arrays 160, 170, 162, 172, 164, 174 and 166 are designated A, B, C, D, E, F and G, respectively, then the output signals on a line-by-line basis are given by the following formula:

$$S_1 = (A_1 - B_1) + (C_2 - D_2) + (E_3 - D_3) + (G_4 - F_4)$$

$$S_2 = (A_2 - B_2) + (C_3 - D_3) + (E_4 - D_4) + (G_5 - F_5) \ldots$$

$$S_n = (A_n - B_n) + (C_{n+1} - D_{n+1}) + (E_{n+2} - D_{n+2}) + (G_{n+3} - F_{n+3})$$

As in the previous embodiment described in reference to FIGS. 11 and 12, the multiplexer 178 includes storage registers for storing and signals after each line exposure until they are combined according to the above formula. Since such multiplexer circuits are well known to those skilled in the art, its description will not be given in greater detail herein. Also, the synchronous indexing of the patient is accomplished as in the embodiment depicted in FIG. 11.

Referring now more particularly to FIG. 14, another alternative embodiment is depicted in which the post-scatter collimator 190 does not have a plurality of slots and a central photo-diode array 212 monitors the flare region. X-ray beam 4 is generated by the x-ray tube 2 to impinge on a pre-scatter collimator 180 having a pair of parallel slots 182 and 184. The collimator 180 thus divides the beam 4 into two x-ray beams 186 and 188. For purposes of explantion, the beams 186 and 188 have been shown as each comprising two hypothetical x-ray beams as indicated by the dashed lines for a total of four beams. The x-ray beams 186 and 188 pass through the patient's body 10 and the post-scatter collimator having a single slot 192 to impinge on the x-ray image intensifier tube 18. The image intensifier tube 18 produces corresponding line images 194, 196, 198 and 200. It must be remembered that the line images 194 and 196 are actually a single, broad line image as are the line images 198 and 200 but for purposes of the operation of the detector system they are treated as being separate. The central flare region 202 divides these wide line images. Photo-diode arrays 204, 206, 208 and 210 monitor these line images and a central photo-diode array 212 monitors the flare region 202 through appropriate optical means 203. The outputs from these photo-diode arrays are supplied to a control circuit 214 which, in turn, provides the difference between these output signals and the output signals of the flare monitoring photo-diode array 212 to a multiplexing circuit 216.

If the outputs from the photo-diode arrays 204, 206, 212, 208 and 210 are labeled A, B, C, D, and E, respectively, and if the signal derived from each hypothetical line on the patient's body is designated S, then S for each line on the patient's body is defined by the following formula:

$$S_1 = (A_1 - C_1) + (B_2 - C_2) + (D_4 - C_4) + (E_5 - C_5)$$

$$S_2 = (A_2 - C_2) + (B_3 - C_3) + (D_5 - C_5) + (E_6 - C_6) \ldots$$

$$S_n = (A_n - C_n) + (B_{n+1} - C_{n+1}) + (D_{n+3} - C_{n+3}) + (E_{n+4} - C_{n+4})$$

The multiplexer 216 includes the appropriate registers for storing these signals so they can be combined in the manner described above. The patient indexing is carried out by the mechanism heretofore described.

Referring now more particularly to FIG. 15, an embodiment in which no flare subtraction takes place is illustrated. In this embodiment flare is compensated for by having an aluminum film covering the output phosphor display screen as described above in reference to FIG. 9. In this embodiment an x-ray tube 2 generates a wide fan beam 4 which passes through a single slit 220 in a pre-scatter collimator 218. For purposes of illustration the fan beam 4 has been divided into seven different hypothetical fan beams as indicated by the dashed lines. This single fan beam 4 passes through the patient's body 10 and through the single slit 224 of a post-scatter collimator 222 to impinge upon the x-ray image intensifier tube 18. The tube 18 is constructed substantially identical to that depicted in FIG. 9, that is, it has a metal foil covering 90 on the vacuum side of the output display screen 26 to substantially eliminate the flare effect.

Although the output screen of tube 18 actually produces a single board line image, this image can be thought of as comprising seven contiguous line segments which are monitored by separate photo-diode arrays 226, 228, 230, 232, 234, 236 and 238 through an appropriate optical focussing system 240. The spacing and size of the photo-diode elements across the width of the patient determine the horizontal resolution of the output image whereas the vertical resolution is defined principally by the resolving power of the x-ray image intensifier tube 18. The spacing between adjacent photo-diode arrays is not terribly critical because the optical system 240 can focus at extremely finite lines upon the output screen of the tube 18.

The outputs of the photo-diode arrays are supplied to a photo-diode control circuit 242 which, in turn, supplies the outputs to a multiplexing circuit 244 which contains the appropriate shift registers as discussed above in reference to the embodiments of FIGS. 11-14. Again, if the outputs of the photo-diode arrays 226-238 can be designated A-G, respectively, and if the output signal for each hypothetical line of the patient's body which is scanned is designated S, then S for each line is defined by the following formula:

$$S_1 = A_1 + B_2 + C_3 + D_4 + E_5 + F_6 + G_7$$

$$S_2 = A_2 + B_3 + C_4 + D_5 + E_6 + F_7 + G_8 \ldots$$

$$S_n = A_n + B_{n+1} + C_{n+2} + D_{n+3} + E_{n+4} + F_{n+5} + G_{n+6}$$

In all of the embodiments depicted in FIGS. 11-15, by arranging the fan beams adjacent to one another, one obtains the economic advantage of using a single image intensifier tube and removes the possible problems, related to the multiplexing method depicted in FIGS. 6 and 7, of matching zones together, such as line 500 with 501, and 1000 with 1001, etc. This is especially true in the embodiment depicted in FIG. 15 where a single continuous fan beam is generated. Also since each hypothetical line is scanned by several detector arrays or fan beams, detector non-uniformity or artifacts are averaged and become less prominent.

One could further reduce x-ray tube heat load by using several groups of adjacent fan beams, each replacing the single fan beam shown in FIGS. 6 and 7.

Although in all of the above described embodiments the output window 24 was described as being glass, part of the flare in the image is caused by light scatter in this output glass window. Therefore a further improvement in all of the foregoing emobdiments, and which is illustrated in FIG. 15, is to substitute for the output glass window a thick, fiberoptical window 246.

In all of the above described embodiments, the construction of the image intensifier tube has been described as being essentially in accordance with the teachings in the applicant's issued U.S. Pat. No. 4,140,900. However, the preferred configuration as depicted in FIG. 1, having a longitudinal dimension much larger than the width and the height of the image intensifier tube, is quite different from the preferred configuration described in U.S. Pat. No. 4,140,900. The difference makes certain design tasks simpler and also makes certain tasks more difficult. For example, the long and narrow input window has very little force on it due to the atmospheric pressure and as a result, alloys of high tensile strength are no longer required. On the other hand, the long and narrow output window requires extremely close matching of the thermal expansion coefficients of the output window glass material and the metal flange material to which the glass must form a vacuum seal. Therefore, yet another embodiment is a proximity image intensifier tube with an essentially all glass envelope, thereby avoiding thermal expansion mismatch problems. Tube elements are suspended in the glass envelope and electrical contact to the elements are provided by several feed-throughs.

Figure 16:
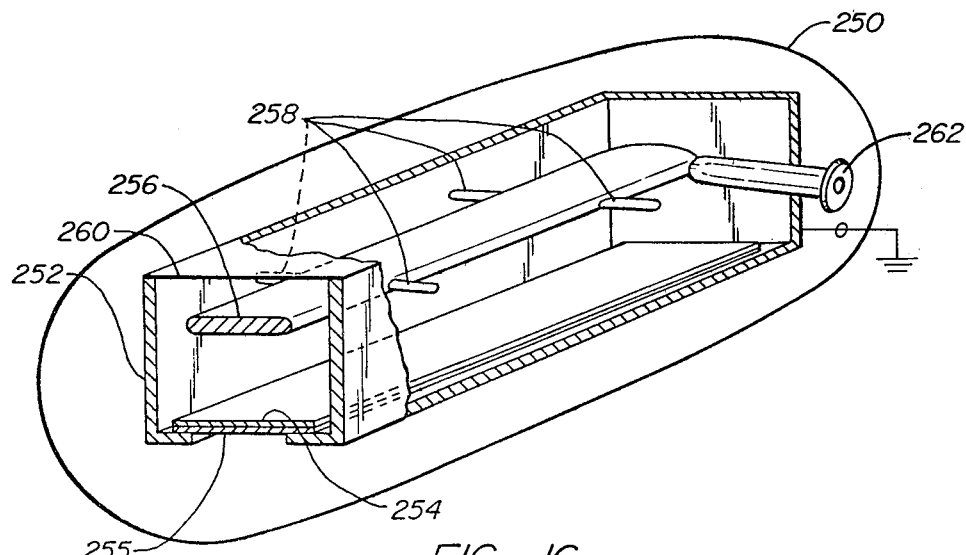
FIG. 16 shows a preferred embodiment of an all glass envelope proximity type image intensifier tube.

Referring now to FIG. 16, a preferred embodiment of an all glass envelope proximity type image intersifier tube is depicted. The image tube is comprised of an essentially all glass envelope 250, an internal metallic structural frame 252 which supports the output phosphor screen 254, a scintillator-photocathode screen assembly 256 with semi-insulating, chrome oxide coated rods 258, and a metallic foil 260 input window. The scintillator-photocathode screen 256 and the output phosphor screen 254 are planar and parallel to each other. The output phosphor screen 254 is comprised of a phosphor layer deposited on a glass or fiberoptical plate 255. The sintillator-photocathode screen 256 is connected to an external, high voltage source (not shown) through a connecting feed through 262, and is normally operated at a higher negative potential. The metal frame 252, the output phosphor screen 254 and the metallic foil 260 are all electrically connected to each other, normally operated at ground potential, and together form an electrical shield around the scintillator-photocathode screen 256 so that the glass envelope 250 would not be charged. Detailed description of the remaining components are given in U.S. Pat. No. 4,140,900.

In all of the embodiments described in reference to FIGS. 11-15, inclusive, it is to be understood that the control unit 48 (depicted in FIG. 1) coordinates the movement of the patient table 14, through the motor means 50, with the scanning of the photo-diode arrays, through the various control circuits 124, 178, 216 and 242, so that the scanning takes place only when the hypothetical exposure lines on the patient 10 are aligned with the fan beams.

However, it should be obvious to those skilled in the art that if the transport speed of the patient's body is precisely known and that it is not exactly indexed to the fan beam spacing, an interpolation formula could be derived to compute $S_n$. For example, if the transport speed in FIG. 15 is exactly one half the spacing between the fan beams per exposure, then $$S_1 = A_1 + \tfrac{1}{2}(A_2 + B_2) + B_3 + \tfrac{1}{2}(B_4 + C_4) + C_5 + \tfrac{1}{2}(C_6 + D_6) + D_7 + \tfrac{1}{2}(D_8 + E_8) + E_9 + \tfrac{1}{2}(E_{10} + F_{10}) + F_{11} + \tfrac{1}{2}(F_{12} + G_{12}) + G_{13}$$

etc.

The terms and expressions which have been employed herein are used as terms of description and not of limitation, and there is no intention, in the use of such terms and expressions of excluding equivalents of the features shown and described, or portions thereof, it being recognized that various modifications are possible within the scope of the invention as claimed.

What is claimed is:

1. An x-ray intensifier detector system for an x-ray fan beam, the detector system comprising:
    an x-ray image intensifier tube having a continuous strip of x-ray input screen and a continuous strip of output phosphor display screen for producing a light strip image representative of the x-ray pattern striking the input screen, the produced image having a longitudinal axis of symmetry,
    a first, scannable, linear array of discrete light detectors arranged in view of the output phosphor display screen for sequentially detecting light generated along the longitudinal axis of the display image on the output phosphor display screen,
    a second, scannable, linear array of discrete light detectors in view of the output phosphor display screen for sequentially detecting light generated on the output phosphor display screen along a hypothetical line which is parallel to the longitudinal axis of the display image and spaced from it by a distance equal to one to ten times the full width at half maxima of the light strip image, the individual detectors of the first and second arrays having a physical correspondence to each other which is determined in part by the sequence in which they are scanned, and a scanning display for displaying the individual differences between the outputs of corresponding detectors of the first and second arrays.

2. The detector system as recited in claim 1 in combination with x-ray fan beam generator means for x-raying a patient and further comprising scanning means for holding the detector system and the x-ray generator means in a predetermined alignment with each other while effecting relative movement between the patient on the one hand and the x-ray generator means and the detector system on the other hand, whereby the patient's body is scanned.

3. The detector system as recited in claim 1 wherein the scanning display comprises a raster scan, video display.

4. The detector system as recited in claim 1 wherein the image intensifier tube is of the proximity type and includes an elongated input window strip, an elongated, planar scintillator strip, an elongated, planar photocathode strip located immediately adjacent to the scintillator strip and between the scintillator strip and the output display screen, an output window immediately adjacent to the display screen, the display screen also being a planar strip, means for providing an electrostatic potential between the phosphor display screen and the photocathode, and an evacuated housing surrounding the scintillator, the photocathode and the display screen which is closed at one end by the input window and which is closed at the other end by the output window.

5. The detector system as recited in claim 4, further comprising a metallic covering for the vacuum side of the display screen, the thickness of the covering being selected to dissipate at least one third of the kinetic energy of photoelectrons passing through it.

6. The detector system as recited in claim 5 wherein the metallic covering consists substantially of aluminum.

7. An x-ray intensifier detector system for detecting an x-ray fan beam, the detector system comprising:
an x-ray image intensifier tube having an input window and a display screen for producing a light strip image representative of the x-ray pattern striking the input screen, the produced image having a longitudinal axis of symmetry, and wherein the image intensifier tube is of the proximity type and includes an elongated input window strip, an elongated, planar scintillator strip, an elongated, planar photocathode strip located immediately adjacent to the scintillator strip and between the scintillator strip and the output display screen, an output window immediately adjacent to the display screen, the display screen also being a planar strip, means for providing an electrostatic potential between the phosphor display screen and the photocathode, an evacuated housing surrounding the scintillator, the photocathode and the display screen which is closed at one end by the input window and which is closed at the other end by the output window, a metallic covering for the vacuum side of the display screen, the metallic covering being thick enough to dissipate at least one third of the kinetic energy of photoelectrons passing through it to strike the display screen;

a first, scannable, linear array of discrete light detectors for sequentially detecting light generated along the longitudinal axis of the display image; and a scanning display for displaying the outputs of the detectors of the first array.

8. The detector system as recited in claim 7 wherein the covering consists substantially of aluminum.

9. In combination, x-ray fan beam generator means for x-raying a patient, and the detector system as recited in claim 7 further comprising a plurality of primary arrays of discrete light detectors, including the first array, which are scannable in a direction parallel to the plane of the fan beam for detecting the display image, means for effecting movement of the patient relative to the fan beam whereby each one of a predetermined number of hypothetical lines running through the patient and transverse to the direction of movement is sequentially aligned over each one of the primary arrays of light detectors, multiplexing means for combining the outputs for each primary array for each hypothetical line to produce line by line sum signals and wherein the scanning display displays the sum signals line by line to form an image.

10. The combination as recited in claim 9 wherein the x-ray generator means generate a plurality of fan beams, each fan beam being aligned with separate predetermined ones of the primary photo-diode arrays, and the intensifier tube produces a plurality of light strip images, each having a separate longitudinal axis of symmetry.

11. The combination as recited in claim 10 further comprising a plurality of secondary arrays of discrete light detectors, which are scannable in a direction parallel to the planes of the fan beams for detecting light generated on the display screen along hypothetical lines which are parallel to the longitudinal axes of the light strip images but spaced from them by predetermined distances, the individual detectors of the primary and secondary arrays having a physical correspondence to each other which is determined in part by the sequence in which they are scanned.

12. The combination as recited in claim 11 further comprising means electrically interposed between the combining means and the primary and secondary arrays for supplying to the combining means the individual differences between the outputs of the corresponding detectors of the first and second arrays.

13. The detector system as recited in claims 4 or 7 wherein the output window is comprised of a fiberoptic plate.

14. An x-ray intensifier detector system for detecting an x-ray fan beam, the detector system comprising:
an x-ray image intensifier tube having a continuous strip of x-ray input screen and a continuous strip of output phosphor display screen for producing a light strip image representative of the x-ray pattern striking the input screen, the produced image having a longitudinal axis of symmetry, a first, scannable, linear array of discrete light detectors in view of the output phosphor display screen for sequentially detecting light generated along the longitudinal axis of the display image on the output phosphor display screen.

a second, scannable, linear array of discrete light detectors in view of the output phosphor display screen for sequentially detecting light generated on the output phosphor display screen along a hypothetical line which is parallel to the longitudinal axis of the display image and spaced from it by a predetermined distance, the individual detectors of the first and second arrays having a physical correspondence to each other which is determined in part by the sequence in which they are scanned, and wherein the detectors of the second array are larger and more light sensitive than the corresponding detectors of the first array, and a scanning display for displaying the individual differences between the outputs of corresponding detectors of the first and second arrays.

15. The detector system as recited in claim 4 wherein the linear array comprises discrete solid state detectors.

16. In combination, a plurality of x-ray intensifier detector systems for detecting an x-ray fan beam, each detector system comprising:

an x-ray image intensifier tube having a continuous strip of x-ray input screen and a continuous strip of output phosphor display screen for producing a light strip image representative of the x-ray pattern striking the input screen, the produced image having a longitudinal axis of symmetry, a first, scannable, linear array of discrete light detectors arranged in view of the output phosphor display screen for sequentially detecting light generated along the longitudinal axis of the display image on the output phosphor display screen, a second, scannable, linear array of discrete light detectors in view of the output phosphor display screen for sequentially detecting light generated on the output phosphor display screen along a hypothetical line which is parallel to the longitudinal axis of the display image and spaced from it by a predetermined distance, the individual detectors of the first and second arrays having a physical correspondence to each other which is determined in part by the sequence in which they are scanned, a scanning display for displaying the individual differences between the outputs of corresponding detectors of the first and second arrays, x-ray fan beam generator means for x-raying a patient by generating a plurality of x-ray fan beams, each fan beam being directed to a separate one of the detector systems, scanning means for holding the detector systems and the x-ray generator means in a predetermined alignment with each other while effecting relative movement between the patient on the one hand and the x-ray generator means and the detector system on the other hand, whereby the patient's body is scanned.

17. The combination as recited in claim 16 wherein the x-ray generator means include a single x-ray tube having a tube focal spot, wherein the plurality of detectors are arranged along hypothetical lines passing through the tube focal spot, and wherein the scanning means rotate the x-ray generator means and the detectors en masse around the tube focal spot in a direction which is perpendicular to the planes of the fan beams.

18. The combination as recited in claim 16 wherein the x-ray generator means generate x-ray fan beams which are plane parallel to each other and wherein the scanning means effect relative movement in a direction which is perpendicular to the planes of the fan beams.

19. An x-ray intensifier detector system for detecting an x-ray fan beam, the detector system comprising:

an x-ray image intensifier tube having a continuous strip of x-ray input screen and a continuous strip of output phosphor display screen for producing a light strip image representative of the x-ray pattern striking the input screen, the produced image having a longitudinal axis of symmetry, a first, scannable, linear array of discrete light detectors for sequentially detecting light generated along the longitudinal axis of the display image, a second, scannable, linear array of discrete light detectors for sequentially detecting light generated on the display screen along a hypothetical line which is parallel to the longitudinal axis of the display image and spaced from it by a predetermined distance, the individual detectors of the first and second arrays having a physical correspondence to each other which is determined in part by the sequence in which they are scanned, a scanning display for displaying the individual differences between the outputs of corresponding detectors of the first and second arrays, and an asymmetric post-scatter collimator, having a slit therein, located in front of the intensifier tube relative to the incoming x-ray beam, the collimator slit having a width which is twice the width of the x-ray fan beam and being placed so that the beam passes asymmetrically through one longitudinal side of the slit.

20. The detector system as recited in claim 19 in combination with a controllable x-ray fan beam generator which can be selectively pulsed on and off and further comprising a prescatter collimator, having a slit therein, and means for oscillating the pre-scatter collimator slit with respect to the beam and in synchronism with the pulsing of the x-ray fan beam generator so that the first and second light detector arrays are alternatingly exposed.

21. An x-ray intensifier detector system for detecting an x-ray fan beam, the detector system comprising:

an x-ray image intensifier tube having an input window and a display screen for producing a light strip image representative of the x-ray pattern striking the input screen, the produced image having a longitudinal axis of symmetry, and wherein the image intensifier tube is of the proximity type and includes an elongated input window strip, an elongated, planar scintillator strip, an elongated, planar photocathode strip located immediately adjacent to the scintillator strip and between the scintillator strip and the output display screen, an output window immediately adjacent to the display screen, the display screen also being a planar strip, means for providing an electrostatic potential between the phosphor display screen and the photocathode, an evacuated housing surrounding the scintillator, the photocathode and the display screen which is closed at one end by the input window and which is closed at the other end by the output window, a metallic covering consisting substantially of aluminum, for the vacuum side of the display screen, wherein the thickness of the metallic covering is defined by:

$$t = (k_1/p)(E/3)k_2$$

where
- t = covering thickness in centimeters (cm)
- $\rho$ = density of covering in grams per cubic centimeter (gm/cm$^3$)
- E = energy of the electron in electron volts (ev)
- $k_1 = 5 \times 10^{-3}$ milligrams/cm$^2$/Kev
- $k_2 = 1.67$ a first, scannable, linear array of discrete light detectors for sequentially detecting light generated along the longitudinal axis of the display image; and a scanning display for displaying the outputs of the detectors of the first array.

22. An x-ray intensifier detector system for an x-ray fan beam, the detector system comprising:

an x-ray image intensifier tube having a continuous strip of x-ray input screen and a continuous strip of output phosphor display screen for producing a light strip image representative of the x-ray pattern striking the input screen, the produced image having a longitudinal axis of symmetry, a post-scatter collimator, having a slit therein, located in front of the intensifier tube relative to the incoming x-ray beam, a first, scannable, linear array of discrete light detectors arranged in view of the output phosphor display screen for sequentially detecting light generated along the longitudinal axis of the display image on the output phosphor display screen, a second, scannable, linear array of discrete light detectors in view of the output phosphor display screen for sequentially detecting light generated on the output phosphor display screen along with a hypothetical line which is parallel to the longitudinal axis of the display image and spaced from it by a predetermined distance, the individual detectors of the first and second arrays having a physical correspondence to each other which is determined in part by the sequence in which they are scanned, and a scanning display for displaying the individual differences between the outputs of corresponding detectors of the first and second arrays.

23. In combination, x-ray fan beam generator means for x-raying a patient, an x-ray image intensifier tube having a continuous strip of x-ray input screen and a continuous strip of output phosphor display screen for producing a light strip image representative of the x-ray pattern striking the input screen, the produced image having a longitudinal axis of symmetry, a first, scannable, linear array of discrete light detectors arranged in view of the output phosphor display screen for sequentially detecting light generated along the longitudinal axis of the display image on the output phosphor display screen, a second, scannable, linear array of discrete light detectors in view of the output phosphor display screen for sequentially detecting light generated on the output phosphor display screen along a hypothetical line which is parallel to the longitudinal axis of the display image and spaced from it by a predetermined distance, the individual detectors of the first and second arrays having a physical correspondence to each other which is determined in part by the sequence in which they are scanned, a plurality of primary arrays of discrete light detectors, including the first array, which are scannable in a direction parallel to the plane of the fan beam for detecting the display image, means for effecting movement of the patient relative to the fan beam whereby each one of a predetermined number of hypothetical lines running through the patient and transverse to the direction of movement is sequentially aligned over each one of the primary arrays of light detectors, multiplexing means for combining the outputs for each primary array for each hypothetical line to produce line by line sum signals, and a scanning display for displaying the individual differences between the outputs of corresponding detectors of the first and second arrays, and wherein the scanning display displays the sum signals line by line to form an image.

* * * * *